(12) United States Patent
Matsuo et al.

(10) Patent No.: US 9,289,498 B2
(45) Date of Patent: Mar. 22, 2016

(54) THICKENING COMPOSITION AND COSMETIC PREPARATION CONTAINING THE SAME

(75) Inventors: Ayano Matsuo, Yakohama (JP); Masayuki Shirao, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 194 days.

(21) Appl. No.: 13/695,022

(22) PCT Filed: Apr. 27, 2011

(86) PCT No.: PCT/JP2011/060262
§ 371 (c)(1),
(2), (4) Date: Mar. 7, 2013

(87) PCT Pub. No.: WO2011/136270
PCT Pub. Date: Nov. 3, 2011

(65) Prior Publication Data
US 2013/0156831 A1  Jun. 20, 2013

(30) Foreign Application Priority Data

Apr. 28, 2010  (JP) ................................. 2010-104081

(51) Int. Cl.
| | |
|---|---|
| *A61K 47/34* | (2006.01) |
| *A61K 47/36* | (2006.01) |
| *A61K 8/73* | (2006.01) |
| *A61K 8/87* | (2006.01) |
| *C08L 5/00* | (2006.01) |
| *C08L 5/04* | (2006.01) |
| *C08L 5/12* | (2006.01) |
| *C08L 89/06* | (2006.01) |
| *A61Q 1/00* | (2006.01) |
| *A61Q 5/06* | (2006.01) |
| *A61K 8/65* | (2006.01) |
| *A61Q 17/04* | (2006.01) |
| *A61Q 19/00* | (2006.01) |
| *A61K 8/04* | (2006.01) |
| *C08G 18/48* | (2006.01) |
| *C08G 18/73* | (2006.01) |
| *C08K 3/22* | (2006.01) |
| *C08L 75/08* | (2006.01) |
| *C08K 5/00* | (2006.01) |

(52) U.S. Cl.
CPC .................. *A61K 47/34* (2013.01); *A61K 8/042* (2013.01); *A61K 8/65* (2013.01); *A61K 8/73* (2013.01); *A61K 8/733* (2013.01); *A61K 8/737* (2013.01); *A61K 8/87* (2013.01); *A61K 47/36* (2013.01); *A61Q 1/00* (2013.01); *A61Q 5/06* (2013.01); *A61Q 17/04* (2013.01); *A61Q 19/00* (2013.01); *C08G 18/4845* (2013.01); *C08G 18/73* (2013.01); *C08L 5/00* (2013.01); *C08L 5/04* (2013.01); *C08L 5/12* (2013.01); *C08L 89/06* (2013.01); *A61K 2800/10* (2013.01); *C08K 3/22* (2013.01); *C08K 5/0008* (2013.01); *C08L 75/08* (2013.01)

(58) Field of Classification Search
None
See application file for complete search history.

(56) References Cited

U.S. PATENT DOCUMENTS

| | | | |
|---|---|---|---|
| 6,440,431 B1 | 8/2002 | Yoshida et al. | |
| 2009/0047312 A1* | 2/2009 | Miyazawa et al. | 424/401 |

FOREIGN PATENT DOCUMENTS

| | | | |
|---|---|---|---|
| EP | 1013264 | * | 6/2000 |
| JP | 2001-276203 | | 10/2001 |

OTHER PUBLICATIONS

Espacenet Bibliographic data for JP 2001-276203 published Oct. 9, 2001, two pages.
International Search Report for corresponding PCT/JP2011/060262 mailed Aug. 16, 2011, three pages.

* cited by examiner

*Primary Examiner* — Brian Gulledge
*Assistant Examiner* — Celeste A. Roney
(74) *Attorney, Agent, or Firm* — Rankin, Hill & Clark LLP

(57) ABSTRACT

To provide a thickening composition which exhibits excellent feelings in use, namely, exhibits excellent freshness, non-stickiness and blend into skin feeling, and does not leave any residue on skin, which can stably keep the viscosity thereof in a low to moderate-level viscosity range and which, even when a salt-type ingredient is incorporated therein, does not undergo viscosity change, and also a cosmetic preparation containing the composition. A thickening composition which comprises (a) from 0.1 to 2% by mass of a specific hydrophobic denatured polyether urethane (associative thickener) and (b) from 0.1 to 2% by mass of a microgel to be obtained by grinding a gel of a hydrophilic compound having a gelling capability, in a ratio of component (a)/component (b) of from 0.1/0.9 to 0.9 to 0.1 (by mass), and which has a viscosity of from 50 to 50,000 mPa·s (with BL-type viscometer, 12 rotations, 25° C.); and a cosmetic preparation containing the thickening composition.

7 Claims, 1 Drawing Sheet

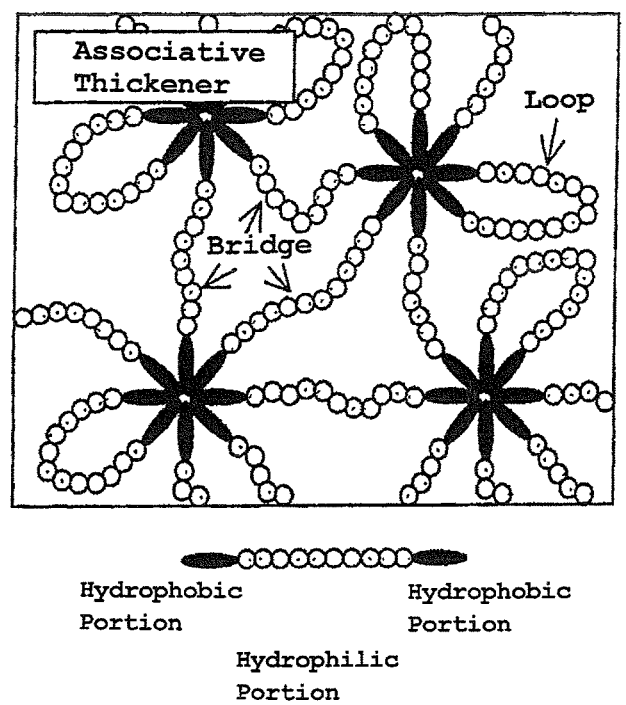

THICKENING COMPOSITION AND COSMETIC PREPARATION CONTAINING THE SAME

TECHNICAL FIELD

The present invention relates to a thickening composition having a low to moderate viscosity and to a cosmetic preparation containing the composition. More precisely, the invention relates to a thickening composition which exhibits excellent feelings in use, namely, exhibits excellent freshness, non-stickiness, and blend into skin feeling, and does not leave any residue on skin, and which can stably keep the viscosity in a low to moderate-level viscosity range, and to a cosmetic preparation containing the composition.

BACKGROUND ART

Heretofore, for thickening cosmetics, there is known to use as a thickener a polysaccharide such as xanthane gum, a hydrophilic synthetic polymer such as polyacrylic acid, and a clay mineral such as bentonite or the like.

However, when using a polysaccharide such as xanthane gum or the like as a thickener in a system containing both a pharmaceutical ingredient and a salt, although it exhibits excellent stability of the system, but is suffers a disadvantage of providing a sticky feeling in use. When in using a hydrophilic synthetic polymer such as polyacrylic acid or the like as a thickener, it exhibits good feeling in use of non-stickiness and freshness; however, if a pharmaceutical ingredient and a salt are highly-incorporated into a system, it occurs a viscosity decrease of the system as the salt tolerance and the ion tolerance thereof are poor. Further, when in using a clay mineral such as bentonite or the like as a thickener, it suffers a disadvantage of providing a feeling of squakiness in use On the other hand, as a water-soluble thickener having an excellent thickening effect, a thickener consists of a hydrophobic denatured polyether urethane (associative polymer) has been developed (Patent Reference 1), and is used in cosmetics (Patent References 2 and 3). That is to say, Patent Reference 2 discloses a cosmetic composition containing a hydrophobic denatured polyether urethane, and a carboxyvinyl polymer and/or xanthane gum; and Patent Reference 3 discloses an external preparation for skin containing a hydrophobic denatured polyurethane and collagen.

Furthermore, as a thickener having a non-stickiness and giving a fresh feeling in use, a microgel has been developed, which is prepared by grinding or crushing a hydrophilic compound gel having a gelling ability, and is used in cosmetics (Patent Reference 4). Other one than the above-mentioned microgel, another type of microgel has been separately developed through radical polymerization of a water-soluble polymerizable monomer; and a thickening composition as well as a cosmetic preparation containing the said radical-polymerized microgel and a hydrophobic denatured polyether urethane is disclosed (Patent Reference 5).

However, each of the compositions and the cosmetics disclosed in the above-mentioned Patent References 2 to 5 is for the purpose of preparing a base having a relatively high viscosity such as a cream-like base or the like. The composition of Patent Reference 2 has a thickening effect and good feelings in use, such as moistness and non-stickiness, but it has not been investigated in point of the viscosity stability thereof in a low to moderate-level viscosity range and of the fresh feeling in use. Also the composition of Patent Reference 3 has a thickening effect and a good feeling of elasticity in use, but has not been investigated in point of the viscosity stability thereof in a low to moderate-level viscosity range and of the fresh feeling in use. The thickener of Patent Reference 4 has a thickening effect and a fresh feeling in use, but has not also been investigated in point of the viscosity stability thereof in a low to moderate-level viscosity range and of the blend into skin feeling thereof. The composition of Patent Reference 5 has a thickening effect, and a new-type feeling (new-type elastic feeling) effect, but has not also been investigated in point of the viscosity stability thereof in a low to moderate-level viscosity range.

PRIOR ART REFERENCES

Patent References

Patent Reference 1: JP 9-71766A
Patent Reference 2: JP 2000-239120A
Patent Reference 3: JP 2005-343841A
Patent Reference 4: JP 2001-342451A
Patent Reference 5: JP 2007-291026A

SUMMARY OF INVENTION

Problems that Invention is to Solve

The present inventors have found that, by combining conventional water-soluble thickeners, a synergistic thickening effect which the individual aqueous solutions could not attain can be obtained, and by utilizing them, a thickening composition can be prepared, which can stably keep the viscosity thereof in a low to moderate-level viscosity range, which is excellent in feelings during and after application thereof, and which, even when a salt-type pharmaceutical ingredient or a salt is incorporated therein, can still exhibit the thickening effect thereof without any influence of the added those ones to the thickening effect of the composition, and upon these findings have completed the present invention.

Therefore, the invention is intended to provide a thickening composition which exhibits excellent feelings in use, namely, exhibits excellent freshness, non-stickiness and blend into skin feeling, and does not leave any residue on skin, which can stably keep the viscosity thereof in a low to moderate-level viscosity range and which, even when a salt-type ingredient is incorporated therein, does not undergo viscosity change, and to provide a cosmetic preparation containing the composition.

Means for Solving the Problems

For solving the above-mentioned problems, the invention provides a thickening composition comprising (a) from 0.1 to 2% by mass of a hydrophobic denatured polyether urethane represented by the following formula (I), and (b) from 0.1 to 2% by mass of a microgel to be obtained by grinding a gel consisting of a hydrophilic compound having a gelling capability, in a ratio of component (a)/component (b) of from 0.1/0.9 to 0.9 to 0.1 (bymass), and which has a viscosity of from 50 to 50,000 mPa·s (with BL-type viscometer, 12 rotations, 25° C.).

(I)

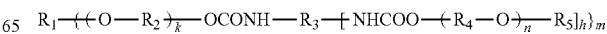

[In the formula (I), $R_1$, $R_2$ and $R_4$ each independently represent an alkylene group having from 2 to 4 carbon atoms, or a phenylethylene group; $R_3$ represents an alkylene group having from 1 to 10 carbon atoms and optionally having an urethane bond; $R_5$ represents a linear, branched or secondary alkyl group having from 8 to 36 carbon atoms; m indicates a number of 2 or more; h indicates a number of 1 or more; k indicates a number of from 1 to 500; and n indicates a number of from 1 to 200.]

The invention also provides the above-mentioned thickening composition in which $R_1$, $R_2$ and $R_4$ in the above-mentioned formula (I) each independently-represent an alkylene group having from 2 to 4 carbon atoms, $R_3$ represents an alkylene group having from 1 to 10 carbon atoms and optionally having an urethane bond, $R_5$ represents a linear, branched or secondary alkyl group having from 12 to 24 carbon atoms, m is 2, h is 1, k is a number of from 100 to 300, and n is a number of from 10 to 100.

The invention also provides the above-mentioned thickening composition in which component (b) is a microgel having a mean particle size of from 0.1 to 1,000 μm, as prepared by grinding a gel formed by dissolving a hydrophilic compound having a gelling capability in water or in an aqueous component followed by keeping it cooled.

The invention also provides the above-mentioned thickening composition in which the hydrophilic compound having a gelling capability is one or more selected from among agar, carrageenan, curdlan, gelatin, gellan gum and alginic acid.

The invention also provides the above-mentioned thickening composition which further contains one or more selected from among pharmaceutical ingredients and salts.

The invention also provides a cosmetic preparation that contains the above-mentioned thickening composition.

Advantageous Effects of Invention

According to the invention, there are provided a thickening composition which exhibits excellent feelings in use, namely, exhibits excellent freshness, non-stickiness and blend into skin feeling, and does not leave any residue on skin, which can stably keep the viscosity thereof in a low to moderate-level viscosity range and which, even when a salt-type ingredient is incorporated therein, does not undergo viscosity change, and also a cosmetic preparation containing the composition.

BRIEF DESCRIPTION OF THE DRAWING

[FIG. 1] It shows an explanatory drawing of the hydrophobic denatured polyether urethane (associative thickener) for use in the invention.

MODE FOR CARRYING OUT THE INVENTION

The invention is described in detail hereinunder.
<Component (a)>

Component (a) for use in the invention is a hydrophobic denatured polyether urethane represented by the following formula (I). The copolymer is an associative thickener. The associative thickener is a copolymer having a hydrophilic portion as the skeleton thereof and hydrophobic portions at the terminals thereof, and the hydrophobic portions of the copolymer are associated with one another to exhibit a thickening effect. In the associative thickener of the type, the hydrophobic portions of the copolymer are associated with one another in an aqueous medium and the hydrophilic portion thereof is in the form of a loop or a bridge, as shown in FIG. 1, thereby exhibiting a thickening effect.

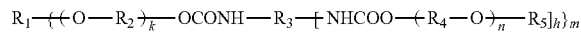

(I)

In the formula (I), $R_1$, $R_2$ and $R_4$ each independently represent an alkylene group having from 2 to 4 carbon atoms, or a phenylethylene group, preferably an alkylene group having from 2 to 4 carbon atoms.

$R_3$ represents an alkylene group having from 1 to 10 carbon atoms and optionally having an urethane bond.

$R_5$ represents a linear, branched or secondary alkyl group having from 8 to 36 carbon atoms, preferably from 12 to 24 carbon atoms.

m indicates a number of 2 or more, preferably 2.

h indicates a number of 1 or more, preferably 1.

k indicates a number of from 1 to 500, preferably a number of from 100 to 300.

n indicates a number of from 1 to 200, preferably a number of from 10 to 100.

The hydrophobic denatured polyether urethane represented by the above-mentioned formula (I) is preferably obtained by, for example, reacting one or more polyether polyols represented by $R_1$—[(O—$R_2$)$_k$—OH]$_m$ (wherein $R_1$, $R_2$, k and m are as defined above) with one or more polyisocyanates represented by $R_3$—(NCO)$_{h+1}$ (wherein $R_3$ and h are as defined above) and one or more polyether monoalcohols represented by HO—($R_4$—O)$_n$—$R_5$ (wherein $R_4$, $R_5$ and n are as defined above).

In this case, $R_1$ to $R_5$ in the formula (I) each is determined by the adopted compounds, i.e. $R_1$—[(O—$R_2$)$_k$—OH]$_m$, $R_3$—(NCO)$_{h+1}$ and HO—($R_4$—O)$_n$—$R_5$ used. Though the ratio of these three compounds is not restricted in particular, it is preferable such that the ratio of the isocyanate group derived from the polyisocyanate to the hydroxyl group derived from the polyether polyol and the polyether monoalcohol, NCO/OH is from 0.8/1 to 1.4/1.

The polyether polyol compound represented by the above-mentioned formula $R_1$—[(O—$R_2$)$_k$—OH]$_m$ can be prepared through addition polymerization of an m-hydric polyol and an alkylene oxide or a styrene oxide, such as propylene oxide, butylene oxide, and epichlorohydrin or the like.

Here the polyol is preferably a dihydric to octahydric one, and exemplary ones include dihydric alcohols, such as ethylene glycol, propylene glycol, butylene glycol, hexamethylene glycol, and neopentyl glycol; trihydric alcohols, such as glycerin, trihydroxyisobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerin, pentaglycerin, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; octahydric alcohols such as sucrose.

$R_2$ is determined owing to the alkylene oxide, styrene oxide or the like to be added. Especially as readily available and for exhibiting the excellent effect, preferred are alkylene oxides having from 2 to 4 carbon atoms or styrene oxide.

The alkylene oxide, styrene oxide or the like to be added may be in the form of homopolymerization or of random polymerization or block polymerization of two or more different types thereof. The addition mode may be any ordinary one. The degree of polymerization k is from 1 to 500. The proportion of the ethylene group that occupies $R_2$'s is preferably from 50 to 100% by mass of all $R_2$'s.

The molecular weight of $R_1$—[(O—$R_2$)$_k$—OH]$_m$ is preferably from 500 to 100,000, more preferably from 1,000 to 50,000.

The polyisocyanate represented by the above-mentioned formula $R_3$—(NCO)$_{h+1}$ may be any one as long as it has at least two isocyanate groups in the molecule. Exemplary ones include aliphatic diisocyanates, aromatic diisocyanates, alicyclic diisocyanates, biphenyl diisocyanates, and phenylmethane di-, tri- and tetra-isocyanates.

Exemplary aliphatic diisocyanates include methylene diisocyanate, dimethylene diisocyanate, trimethylene diisocyanate, tetramethylene diisocyanate, pentamethylene diisocyanate, hexamethylene diisocyanate, dipropylether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butylene glycol dipropyl ether diisocyanate, thiodihexyl diisocyanate, metaxylylene diisocyanate, paraxylylene diisocyanate, and tetramethylxylylene diisocyanate Exemplary aromatic diisocyanates include metaphenylene diisocyanate, paraphenylene diisocyanate, 2,4-tolylene diisocyanate, 2,6-tolylene diisocyanate, dimethylbenzene diisocyanate, ethylbenzene diisocyanate, isopropylbenzene diisocyanate, tolidinediisocyanate, 1,4-naphthalene diisocyanate, 1,5-naphthalene diisocyanate, 2,6-naphthalene diisocyanate, and 2,7-naphthalene diisocyanate.

Exemplary alicyclic diisocyanates include hydrogenated xylylene diisocyanate, and isophorone diisocyanate.

Exemplary biphenyl diisocyanates include biphenyl diisocyanate, 3,3'-dimethylbiphenyl diisocyanate; and 3,3'-dimethoxybiphenyl diisocyanate.

Exemplary phenylmethane diisocyanates include diphenylmethane 4,4'-diisocyanate, 2,2'-dimethyldiphenylmethane 4,4'-diisocyanate, diphenylmethane 4,4'-diisocyanate, 2,5,2',5'-tetramethylphenylmethane 4,4'-diisocyanate, cyclohexylbis(4-isocyanatophenyl)methane, 3,3'-dimethoxydiphenylmethane 4,4'-diisocyanate, 4,4'-dimethoxydiphenylmethane 3,3'-diisocyanate, 4,4'-diethoxydiphenylmethane 3,3'-diisocyanate, 2,2'-dimethyl-5,5'-dimethoxydiphenylmethane 4,4'-diisocyanate, 3,3'-dichlorodiphenyldimethylmethane 4,4'-diisocyanate, and benzophenone 3,3'-diisocyanate.

Exemplary phenylmethane triisocyanates include 1-methylbenzene-2,4,6-triisocyanate, 1,3,5-trimethylbenzene-2,4,6-triisocyanate, 1,3,7-naphthalene triisocyanate, biphenyl-2,4,4'-triisocyanate, diphenylmethane-2,4,4'-triisocyanate, 3-methyldiphenylmethane-4,6,4'-triisocyanate, triphenylmethane-4,4',4"-triisocyanate, 1,6,11-undecane triisocyanate, 1,8-diisocyanate-4-isocyanate-methyloctane, 1,3,6-hexamethylene triisocyanate, bicycloheptane triisocyanate, and tris(isocyanatophenyl) thiophosphate.

Also usable here are dimers and trimers (with isocyanurate bond) of those polyisocyanate compounds; and also usable are biuret compounds thereof as reacted with amines.

Also usable are polyisocyanates having an urethane bond, which are prepared by reacting these polyisocyanate compounds with polyols. As the polyols, preferred are dihydric to octahydric ones. The above-mentioned polyols are preferred.

In the case where a trihydric or more polyhydric polyisocyanate is used as $R_3$—(NCO)$_{h+1}$, preferred are those urethane bond-having polyisocyanates.

The polyether monoalcohol represented by the above-mentioned formula HO—($R_4$—O)$_n$—$R_5$ is not restricted in particular as long as the polyether monoalcohol is a linear, branched or secondary monohydric alcohol polyether. The compound of the type is obtainable by addition polymerization of a linear, branched or secondary monoalcohol with an alkylene oxide, styrene oxide or the like such as ethylene oxide, propylene oxide, butylene oxide, and epichlorohydrin, etc.

The linear alcohol as referred to herein is one represented by the following formula (II).

$R_6$—OH                                                             (II)

The branched alcohol is represented by the following formula (III).

The secondary alcohol is represented by the following formula (IV).

Accordingly, $R_5$ is a residue of the above-mentioned formulae (II) to (IV) as derived by removing the hydroxyl group therefrom. In the formulae (II) to (IV), $R_6$, $R_7$, $R_8$, $R_{10}$ and $R_{11}$ each represent a hydrocarbon group or a fluorocarbon group, and it includes, for example, an alkyl group, an alkenyl group, an alkylaryl group, a cycloalkyl group, and a cycloalkenyl group.

Exemplary alkyl group includes methyl, ethyl, propyl, isopropyl, butyl, isobutyl, tertiary butyl, pentyl, isopentyl, neopentyl, tertiary pentyl, hexyl, heptyl, octyl, 2-ethylhexyl, nonyl, decyl, undecyl, dodecyl, tridecyl, isotridecyl, myristyl, palmityl, stearyl, isostearyl, eicosyl, docosyl, tetracosyl, triacontyl, 2-octyldodecyl, 2-dodecylhexadecyl, 2-tetradecyloctadecyl, and monomethyl-branched isostearyl.

Exemplary alkenyl group includes vinyl, allyl, propenyl, isopropenyl, butenyl, pentenyl, isopentenyl, hexenyl, heptenyl, octenyl, nonenyl, decenyl, undecenyl, dodecenyl, tetradecenyl, and oleyl.

Exemplary alkylaryl group includes phenyl, toluoyl, xylyl, cumenyl, mesityl, benzyl, phenethyl, styryl, cinnamoyl, benzhydryl, trityl, ethylphenyl, propylphenyl, butylphenyl, pentylphenyl, hexylphenyl, heptylphenyl, octylphenyl, nonylphenyl, α-naphthyl, and β-naphthyl.

Exemplary cycloalkyl group and the cycloalkenyl group include cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

In the above formula (III), $R_9$ represents a hydrocarbon group or a fluorocarbon group, and it includes, for example, an alkylene group, an alkenylene group, an alkylarylene group, a cycloalkylene group, and a cycloalkenylene group.

$R_5$ represents a hydrocarbon group or a fluorocarbon group, and is preferably an alkyl group; and more preferably, the total number of the carbon atoms constituting the group is from 8 to 36, even more preferably from 12 to 24.

The alkylene oxide, styrene oxide or the like to be added may be in the form of homopolymerization or of a random polymerization or block polymerization of two or more different types thereof. The addition mode may be any ordinary one. The degree of polymerization n is from 0 to 1000, preferably from 1 to 200, more preferably from 10 to 200. The proportion of the ethylene group that occupies $R_4$'s is preferably from 50 to 100% by weight of all $R_4$'s, more preferably from 65 to 100% by weight. The preferred embodiment gives an associative thickener good for the object of the invention.

For producing the copolymer represented by the formula (I), the compounds may be reacted in the same manner as that for ordinary reaction of polyether and isocyanate, for example, by heating at 80 to 90° C. for 1 to 3 hours.

In reacting the polyether polyol (A) represented by $R_1$—[(O—$R_2$)$_k$—OH]$_m$, the polyisocyanate (B) represented by $R_3$—(NCO)$_{h+1}$ and the polyether monoalcohol (C) represented by HO—($R_4$—O)$_n$—$R_5$, any others may be generated as side products than the copolymer having the structure of the formula (I). For example, in the case where a diisocyanate is used, the main product is the C-B-A-B-C type copolymer represented by the formula (I), and in addition thereto, other copolymers such as C-B-C type one, C-B-(A-B)$_x$-A-B-C type one and the like may be generated as side products. In this case, without particularly separating the copolymer of the type of the formula (I), a mixture that contains the copolymer of the type of the formula (I) may be used in the invention.

In the invention, a commercial product may be used as component (a). As the commercial product, "Adekanol GT-700" (by ADEKA CORPORATION), etc., are exemplified.

The amount of component (a) to be incorporated in the thickening composition of the invention is from 0.1 to 2% by mass, preferably from 0.2 to 1.5% by mass. When the amount is less than 0.1% by mass, then the effect of component (a) cannot be obtained; but on the other hand, when more than 2% by mass, then the viscosity may increase too high and the efficiency in producing the composition may lower, and it occasionally occur sticky feeling in use.

<Component (b)>

As a microgel of component (b) obtained by grinding or crushing a gel of a hydrophilic compound having a gelling capability, it is preferably used in the present invention a microgel having a mean particle size of from 0.1 to 1,000 μm, as prepared by grinding or crushing a gel formed by dissolving a hydrophilic compound having a gelling capability in water or in an aqueous component followed by keeping it cooled.

The hydrophilic compound having a gelling capability is not restricted in particular as long it is a water-soluble compound having a gelling capability and capable of being used in the field of cosmetics and drugs. Concretely, exemplified ones include hydrophilic proteins having a gelling capability, such as gelatin, and collagen; hydrophilic polysaccharides, such as agar, curdlan, scleroglucan, sizofuran, gellan gum, alginic acid, carrageenan, mannan, pectin, and hyaluronic acid. Among above all, especially preferred for use herein are gelatin, agar, curdlan, gellan gum, alginic acid and carrageenan, as hardly influenced by salts and ions and capable of forming a stable gel. One or more hydrophilic compounds having a gelling capability can be used here.

The hydrophilic compound having a gelling capability is dissolved in water or in an aqueous component, then left cooled and solidified to form a gel. The compound may be dissolved in water or in an aqueous component by mixing, heating or the like.

For gelation (solidification), heating the system may be stopped after dissolving it, and then the system is left as such (statically kept as such) until it could be cooled to a temperature lower than the gelling temperature (solidifying temperature) thereof.

The aqueous component may be any one usable in the field of cosmetics and drugs. The component may contain a glycol, such as 1,3-butylene glycol, propylene glycol or the like, or a lower alcohol, such as ethanol, propanol or the like, and in addition thereto, any other ingredient capable of being generally incorporated as an aqueous phase ingredient in cosmetics. For such ingredient, a chelating agent such as metaphosphate salts, edetate salts and others, and a pH controlling agent, and a preservative, etc., are exemplified, but not limited thereto. In the case where gellan gum is used as the hydrophilic compound having a gelling capability, a cation is preferably added to the aqueous component for further enhancing the gel strength. The cation is preferably a monovalent or divalent cation, but not limited thereto. In concrete terms, an acid capable of releasing a monovalent cation ($H^+$) (e.g., acetic acid, citric acid, etc.) or a salt capable of releasing a monovalent or divalent cation, for example, $Mg^{++}$, $Ca^{++}$, $Na^+$ or $K^+$ (e.g., magnesium chloride, calcium chloride, sodium chloride, potassium chloride, etc.) may be added to the component.

The gel strength is not specifically defined, so long as it may be on such a level that the gel itself can sustain the shape thereof and can form a microgel in the next step. In the invention, a gel having a considerably high gel strength can be used, and for example, a gel having a high jelly strength of about 1,000 g/cm$^2$ (as measured according to the method of Agar and Marine Products Guild of Japan) or less may be used, but on the other hand, a gel having a considerably low gel strength of a jelly strength 30 g/cm$^2$ or so may give a microgel for use herein. From the viewpoint of improving the feeling in use, preferred is a gel having a jelly strength of 100 g/cm$^2$ or so.

Combined with the above-mentioned hydrophilic compound having a gelling capability, also usable here is a thickening compound not having a gelling capability for the purpose of modifying the feeling in use. Exemplary thickening compound not having a gelling capability includes hydrophilic synthetic polymers, such as typically polyacrylic acid, polyethylene glycol, polyacrylamide, polyalkylacrylamide/polyacrylamide copolymer, carboxymethyl cellulose, cationated cellulose, and pluronic, as well as hydrophilic natural polymers, such as typically xanthan gum, succinoglycan, gar gum, locust bean gum, and also hydrophilic clay minerals, such as laponite, bentonite, and smectite. Salts of these compounds are also usable here. Additionally using the hydrophilic thickening compound not having a gelling capability makes it possible to control the gel strength of the gel to be obtained in any desired manner. When the proportion of the thickening compound not having a gelling capability is increased, then the gel strength lowers. One or more of such thickening compounds not having a gelling capability may be used here.

The proportion of the hydrophilic thickening compound not having a gelling capability to be incorporated here may be, but not limited thereto, from 1 to 100% by weight or so of the hydrophilic compound having a gelling capability.

Next, the formed gel is ground or crushed with a homogenizer, a disperser, a mechanical stirrer or the like to give a desired microgel. In the invention, the mean particle size of the microgel is from 0.1 to 1,000 µm, preferably from 1 to 300 µm or so, more preferably from 10 to 200 µm or so. When the mean particle size of the microgel is more than 1,000 µm, then the usability of the composition would be problematic in such that it tends to hard to pick off the composition to fingers. On the other hand, when less than 0.1 µm, then the composition could not sustain the viscosity thereof as a gel preparation. The degree of grinding or crushing may be suitably controlled in accordance with the intended object of the composition, for example, to such a level that the mean particle size of the microgel to be obtained does not overstep the above-mentioned range of the invention. In the case where a smoother usability of the Composition is required, the gel is more sufficiently ground through high-speed stirring to give a microgel having a smaller particle size, but on the other hand, in the case where a good feeling of the microgel itself is desired, the degree of grinding or crushing may be lowered by slight stirring to give a microgel having a relatively large particle size.

The necessary viscosity of the microgel thus obtained varies depending on the intended use thereof, and therefore could not be defined indiscriminately. For example, when agar is used in a concentration of from 0.5 to 2% or so, the microgel viscosity is preferably from 2,000 to 1,000,000 mPa·s or so as measured with a BL-type viscometer (12 rotations, 25° C.).

The amount of component (b) to be incorporated in the thickening composition of the invention is from 0.1 to 2% by mass, preferably from 0.2 to 2% by mass. When the amount is less than 0.1% by mass, then the effect of component (b) cannot be obtained; but on the other hand, when more than 2% by mass, then it occasionally occur the sticky feeling in use.

In the invention, the blend ratio (by mass) of component (a) to component (b), (a)/(b) is from 0.1/0.9 to 0.9/0.1, preferably from 0.2/0.8 to 0.8/0.2. When the blend ratio is larger than the above range, then it would impair the fresh feeling in use, but on the other hand, when smaller than the range, it could not stably secure the viscosity of the composition and would be therefore unfavorable.

In the invention, by combining the above-mentioned component (a) and component (b), there can be provided a thickening composition having excellent feelings in use, namely excellent freshness and blend into skin feeling not leaving any residue on the skin; and as compared with the case of individually using component (a) or component (b) separately from each other, the thickening effect of the composition of the present case of using the two simultaneously has greatly increased. To that effect, the thickening effect of the composition can be greatly increased, and therefore, component (a) and component (b) may be incorporated in the composition both in a low content therein, thereby stably securing the viscosity of the composition to fall within a low to moderate-level viscosity range. In ordinary compositions, the change in the amount of the thickening ingredient (thickener) to be incorporated therein brings about a logarithmic change in the viscosity of the composition. Consequently, even when the amount of the thickener to be incorporated in the composition is changed only slightly, the viscosity of the composition may greatly change. Specifically, in the case where a thickener having a high thickening capability is used alone, the system viscosity of the composition may be extremely low (for example, like the viscosity of an aqueous solution), or may often tend to increase (for example, like the composition of a creamy to viscous liquid), and it is extremely difficult to stably keep the system viscosity of the composition falling within a low to moderate-level viscosity range (for instance, the composition displays fluidity in a thick gel state when being picked up by fingers or hands). Given the situation, the present inventors tried to combine thickeners having a high thickening capability in an extremely low blend ratio (at a concentration not enough for the thickening effect), thereby stably keeping the viscosity of the composition in a low to moderate-level viscosity range. In the present invention, component (a) and component (b) are combined to exhibit a synergistic thickening effect of the two; and consequently, by combining the two components, it has become possible to easily keep the system viscosity falling within a low to moderate-level viscosity range in a simplified manner.

Concretely, it is desirable that the viscosity of the composition of the invention falls within a low to moderate-level viscosity range of from 50 to 50,000 mPa·s (with B-type viscometer at 25° C.), more preferably from 100 to 30,000 mPa·s.

Another advantage of the thickening composition of the invention is that even when a pharmaceutical ingredient and a salt are incorporated therein, the composition does not undergo viscosity decrease. The pharmaceutical ingredient and the salt may be any of water-soluble or oil-soluble ones.

Exemplary pharmaceutical ingredient includes vitamins, antiinflammatory agents, and antimicrobials. Specific examples of the pharmcaceutical ingredient include vitamins and their derivatives such as vitamin B, P, water-soluble vitamin A, D, etc.; pantothenyl ethyl ether, calcium pantothenate, glycyrrhizinic acid, glycyrrhizinate salts, glycyrrhetinic acid, glycyrrhetinate salts, royal jelly, polyphenol, nicotinic acid and its derivatives (e.g., nicotinamide), resorcinol and its derivatives, sulfur, salicylic acid and its derivatives, alkoxysalicylic acid and its salts, L-ascorbic acid and its derivatives, tranexamic acid and its derivatives, glucoside, urea, xylitol, trehalose, and caffeine.

Exemplary salt includes organic acid salts, amino acid salts, and inorganic salts: Examples of the organic acid salts include hydrochlorides, metal salts (sodium salts, potassium salts), amine salts of citric acid, lactic acid, oxalic acid, and sulfonic acid. Examples of the amino acid salts include chlorides, metal salts (sodium salts, potassium salts), amine salts of glycine, alanine, proline, lysine, aspartic acid, and glutamic acid. Examples of the inorganic salts include sodium, potassium, magnesium, calcium and the like carbonates, phosphates, nitrates, borates, sulfates, sulfites, and halides (sodium chloride, potassium chloride).

The thickener in the invention and the cosmetic preparation that contains the thickener both have excellent salt tolerance, and even when a salt or the above-mentioned pharmaceutical ingredient in the form of a salt thereof is incorporated therein, the system stability of the resulting composition is not influenced by any other ingredients simultaneously incorporated therein, and the composition keeps excellent feeling in use.

Heretofore, a compound having a gelling capability, such as agar, carrageenan, curdlan, gelatin or the like has been used as a thickener, but in such a case, the compound is heated, dissolved and gradually cooled with stirring to give a viscous liquid with no solidification (gelation) (for example, JP-11-209262A). However, in the case where a compound having a gelling capability is gradually cooled with stirring to give a thickener according to the above-mentioned conventional method, the system thickening degree is limited. In particular, when a pharmaceutical ingredient or a salt is incorporated, the viscosity of the resulting system lowers.

As opposed to this, in the invention, a microgel prepared by once completely gelling (solidifying) the compound and then grinding or crushing it is used as a thickener. The thickener in the invention thus prepared in the manner as above is not one that exhibits the thickening effect owing to the molecular-level entangling, different from thickening polysaccharides or synthetic polymer thickeners heretofore used in ordinary cosmetics, but is one that exhibits the thickening effect owing to the friction of the microgel particles formed by grinding a gel. Accordingly, the thickener in the invention is quite free from a trouble of stickiness that is characteristic of polymer solutions, and can realize an extremely fresh feeling in use. Polymer solutions may undergo viscosity reduction as influenced by the pharmaceutical ingredient or the salt incorporated therein, and therefore incorporation of such a pharmaceutical ingredient or a salt is often limited in the art. However, the invention is free from the problem and can therefore extend the forms in formulation of cosmetics, etc.

In the case where a water-soluble pharmaceutical ingredient or salt is used in the invention, the ingredient or salt may be dissolved in water or in an aqueous component along with the hydrophilic component having a gelling capability to be therein, then kept cooled and solidified to form a gel, and thereafter the gel may be ground to give a microgel; or after the hydrophilic component having a gelling capability may be first dissolved in water or in an aqueous component, then kept cooled and solidified to give a gel, then the gel is ground into a microgel, and thereafter the resulting microgel may be mixed with the pharmaceutical ingredient or the salt.

On the other hand, in the case where the pharmaceutical ingredient or the salt to be used is an oil-soluble one, one preferred embodiment of using the oil-soluble ingredient or salt is as follows: The hydrophilic component having a gelling capability is first dissolved in water or in an aqueous component, then left cooled and solidified to give a gel, and the gel is ground into a microgel, while on the other hand and apart from this, the oil-soluble pharmaceutical ingredient or salt is pre-emulsified in an aqueous phase along with any other oily component to be therein, and thereafter the pre-emulsified mixture is further mixed with the above-mentioned microgel and emulsified to give the intended composition.

In the case where the thickening composition obtained according to the invention is used as a cosmetic, or is incorporated in a cosmetic, in general, additive ingredients capable of being incorporated in cosmetics, for example, moisturizer, preservative, powder, dye, fragrance, pH controlling agent and the like may be suitably incorporated therein within a range not detracting from the object and the advantage of the invention. Preferred examples of the form of the cosmetic include somewhat thick gels, emulsions, etc. Specific examples of the cosmetics to which the invention is preferably applied include moisturizing gel, massage gel, beauty essence, skin lotion, milk, makeup cosmetics, sunscreen goods, hair-care cosmetics such as hair-set agent, hair gel, etc., as well as hair-dye, and body-care goods.

Using the thickening composition obtained according to the invention as a cosmetic preparation makes it possible to greatly increase the thickening capability of the cosmetic and improve the feelings of the cosmetic in use. In addition, even when a pharmaceutical ingredient and a salt are incorporated in the cosmetic preparation in a high ratio, or for example, when the ingredient or salt is incorporated therein in a ratio of about 20% by mass of the entire amount of the cosmetic preparation, there occurs no trouble of system viscosity reduction, and the cosmetic preparation can still keep the system viscosity thereof. Moreover, the cosmetic preparation is stable for a long period of time, not causing water release therefrom. Preferably, the pharmaceutical ingredient or the salt to be incorporated in the composition is at least 0.1% by weight or so of the entire amount of the cosmetic preparation for the purpose of securing the intended effect of the additive incorporation.

EXAMPLES

The invention is described further concretely with reference to the following Examples, by which, however, the invention is not whatsoever limited. Unless otherwise specifically indicated, the incorporated amount is all in terms of % by mass.

In the following Examples, the compounds mentioned below were used for the constituent components.

Hydrophobic Denatured Polyether Urethane [Component (a)]:

A copolymer represented by the above-mentioned formula (I), wherein $R_1$, $R_2$ and $R_4$ each are an ethylene group, $R_3$=hexamethylene group, $R_5$=2-dodecyldodecyl group, h=1, m=2, k=120, n=20, was used ("Adekanol GT-700" by ADEKA CORPORATION).

Agar Microgel [Component (b)]:

An aqueous dispersion of 2% agar was heated at 90° C., and after its complete dissolution was confirmed, this was statically left as such to give a nonflowing gel composition. The gel was ground with a homogenizer to give an agar microgel (having a mean particle size of about 50 μm) for use herein.

Gellari Gum Microgel [Component (b)]:

An aqueous dispersion of 1% gellan gum was heated at 80° C., and after its complete dissolution was confirmed, an aqueous solution of 2.8% sodium chloride was added thereto and uniformly stirred, and statically left as such to give a nonflowing gel composition. The gel was ground with a homogenizer to give a gellan gum microgel (having a mean particle size of about 50 μm) for use herein.

Example 1

Thickening Synergistic Effect and Salt-tolerant Effect by Combination of Component (a) and Component (b)

First, the following test was carried out for confirming the thickening synergistic effect and the salt-tolerant effect by combination of component (a) and component (b) for use in the invention.

Component (a) and component (b) were added to pure water each in the amount indicated in Tables 1 and 2 shown below to prepare an aqueous solution, and then after this was left at room temperature (25° C.) for 1 minute, the viscosity (mPa·s) thereof was measured with a BL-type viscometer (rotor No. 3, 12 rotations).

A salt was added to the sample prepared in the above, and mixed by stirring. This was left at room temperature (25° C.) for 1 minute, and the viscosity (mPa·s) thereof after salt addition was measured with a BL-type viscometer (rotor No. 3, 12 rotations). The salt tolerance of in point of viscosity change was thereby evaluated. The results are shown in Tables 1 to 2.

TABLE 1

| | Composition 1 | Composition 2 | Composition 3 | Composition 4 | Composition 5 | Composition 6 |
|---|---|---|---|---|---|---|
| Hydrophobic denatured polyether urethane | 0.5 | 1.0 | — | — | 0.5 | 1.0 |
| Agar microgel | — | — | 0.5 | 1.0 | 1.0 | 1.0 |
| Pure water | bal. | bal. | bal. | bal. | bal. | bal. |
| Viscosity | 50 | 2350 | 40 | 730 | 4510 | 14550 |

TABLE 1-continued (mPa · s/25° C.)

|  | Composition 7 | Composition 8 | Composition 5 | Composition 9 | Composition 10 |
|---|---|---|---|---|---|
| Hydrophobic denatured polyether urethane | 0.3 | 0.4 | 0.5 | 0.6 | 0.7 |
| Agar microgel | 0.6 | 0.8 | 1.0 | 1.2 | 1.4 |
| Pure water | bal. | bal. | bal. | bal. | bal. |
| Viscosity (mPa · s/25° C.) | 100 | 710 | 4510 | 13450 | 36100 |

|  | Composition 8 | Composition 11 | Composition 5 | Composition 12 |
|---|---|---|---|---|
| Hydrophobic denatured polyether urethane | 0.4 | 0.4 | 0.5 | 0.5 |
| Agar microgel | 0.8 | 0.8 | 1.0 | 1.0 |
| Sodium chloride | — | 1.0 | — | 1.0 |
| Pure water | bal. | bal. | bal. | bal. |
| Viscosity (mPa · s/25° C.) | 710 | 680 | 4510 | 4800 |

TABLE 2

|  | Composition 13 | Composition 14 | Composition 15 |
|---|---|---|---|
| Hydrophobic denatured polyether urethane | 1.0 | — | 0.8 |
| Gellan gum micro gel | — | 0.4 | 0.4 |
| Pure water | bal. | bal. | bal. |
| Viscosity (mPa · s/25° C.) | 2350 | 2950 | 6500 |

|  | Composition 16 | Composition 17 | Composition 18 | Composition 19 | Composition 15 |
|---|---|---|---|---|---|
| Hydrophobic denatured polyether urethane | 0.2 | 0.4 | 0.5 | 0.6 | 0.8 |
| Gellan gum micro gel | 0.1 | 0.2 | 0.25 | 0.3 | 0.4 |
| Pure water | bal. | bal. | bal. | bal. | bal. |
| Viscosity (mPa · s/25° C.) | 75 | 250 | 670 | 2150 | 6500 |

|  | Composition 18 | Composition 20 | Composition 21 | Composition 22 |
|---|---|---|---|---|
| Hydrophobic denatured polyether urethane | 0.5 | 0.5 | 0.8 | 0.8 |
| Gellan gum micro gel | 0.25 | 0.25 | 0.25 | 0.25 |
| Sodium chloride | — | 1.0 | — | 1.0 |
| Pure water | bal. | bal. | bal. | bal. |
| Viscosity (mPa · s/25° C.) | 670 | 820 | 5200 | 5200 |

As obvious from the results shown in Tables 1 to 2, for example, from the comparison of the compositions 1 and 4 with the composition 5, the comparison of the compositions 2 and 4 with the composition 6, and the comparison of the compositions 13 and 14 with the composition 15, it has been confirmed that the combination of component (a) and component (b) significantly increased the thickening effect as compared with the effect of the compositions containing any of component (a) or component (b) alone.

As obvious from the comparison between the compositions 8 and 11, the comparison between the compositions 5 and 12, the comparison between the compositions 18 and 20 and the comparison between the compositions 21 and 22, it has also been confirmed that the combination provides an excellent salt-tolerant effect.

Examples 2 to 3 Comparative Examples 1 to 5

Feelings in Use

Samples having the composition shown in Tables 3 and 4 below were prepared. The samples were tested for the feelings thereof in use according to the evaluation standards mentioned below. The results are shown in Table 5.

[Feelings in Use During Application to Skin (Freshness, Non-Stickiness, Blend into Skin Feeling, Absence of Residue on Skin With no Twisting)]

Expert panelists (10 women) tried the samples (compositions) of Examples and Comparative Examples, and evaluated them in point of the feelings in use during application thereof to the skin, namely in point of the freshness, the non-stickiness, the blend into skin feeling and the absence of residue on the skin (with no twisting), according to the evaluation standards mentioned below.

(Evaluation)

⊙: 8 or more panelists answered that the feelings in use were excellent.

○: From 6 to 7 panelists answered that the feelings in use were excellent.

Δ: From 3 to 5 panelists answered that the feelings in use were excellent.

x: 2 or less panelists answered that the feelings in use were excellent.

TABLE 3

| Cosmetics (Ingredients compounded) | Amount |
|---|---|
| Glycerin | 3 |
| 1,3-Butylene glycol | 5 |
| Ethanol | 5 |
| Citric acid | 0.01 |
| Sodium citrate | 0.09 |
| Disodium edetate | 0.05 |
| Phenoxyethanol | 0.35 |
| Potassium 4-methoxysalicylate | 1 |
| Acrylic acid/alkyl methacrylate copolymer | 0.05 |
| Potassium hydroxide | 0.1 |
| Dimethylpolysiloxane | 2.5 |
| Thickening agent/thickening composition indicated in Table 4 | Amount indicated in Table 4 |
| Pure water | bal. |

TABLE 4

|  | Thickening agent/thickening composition | Amount |
|---|---|---|
| Comparative Example 1 | Hydrophobic denatured polyether urethane | 0.5 |
| Comparative Example 2 | Agar microgel | 1 |
| Example 2 | Hydrophobic denatured polyether urethane (0.4% by mass) + Agar microgel (0.8% by mass) | 1.2 |
| Comparative Example 3 | Gellan gum microgel | 0.25 |
| Example 3 | Hydrophobic denatured polyether urethane (0.5% by mass) + Gellan gum microgel (0.25% by mass) | 0.75 |
| Comparative Example 4 | Hydrophobic denatured polyether urethane (1% by mass) + Carboxyvinyl polymer (0.25% by mass) | 1.25 |
| Comparative Example 5 | Hydrophobic denatured polyether urethane (1% by mass) + Xanthane gum (0.1% by mass) | 1.1 |

TABLE 5

| | Freshness | Non Stickiness | Blend into skin feeling | Absence of residue on skin |
|---|---|---|---|---|
| Comparative Example 1 | X | Δ | ⊙ | ⊙ |
| Comparative Example 2 | ⊙ | ○ | X | X |
| Example 2 | ⊙ | ○ | ⊙ | ⊙ |
| Comparative Example 3 | ⊙ | ○ | X | X |
| Example 3 | ⊙ | ○ | ⊙ | ⊙ |
| Comparative Example 4 | X | ○ | ○ | Δ |
| Comparative Example 5 | X | ○ | ○ | ○ |

As obvious from the results shown in Table 5, it has been confirmed that the combination of component (a) and component (b) incorporated in the cosmetics provides excellent feelings in use, as compared with the cosmetics comprising any of component (a) or component (b) alone as the thickener therein (comparison between Example 2 and Comparative Example 2, comparison between Example 3 and Comparative Example 3). Comparative Examples 4 and 5 are compositions shown in "Patent Reference 2" (prior art reference). The samples of these Comparative Examples 4 and 5 were good in point of the feelings in use, namely, in point of moistness and non-stickiness; however, the samples of Examples 2 and 3 were better than these in point of the comprehensive evaluation of feelings in use.

Formulation Examples of the invention are shown below.

Formulation Example 1

Skin Milk

| (Constitutive Ingredients) | (% by mass) |
|---|---|
| (1) Dimethylpolysiloxane | 2 |
| (2) Behenyl alcohol | 1 |
| (3) Batyl alcohol | 0.5 |
| (4) Glycerin | 5 |
| (5) 1,3-Butylene glycol | 7 |
| (6) Erythritol | 2 |
| (7) Hardened oil | 3 |
| (8) Squalane | 6 |
| (9) Pentaerythritol tetra-2-ethylhexanoate | 2 |
| (10) Polyoxyethylene glyceryl isostearate | 1 |
| (11) Polyoxyethylene glyceryl monostearate | 1 |
| (12) Sodium hexametaphosphate | 0.05 |
| (13) Phenoxyethanol | q. s. |
| (14) Hydrophobic denatured polyether urethane | 0.4 |
| (15) Agar microgel | 0.8 |
| (16) Pure water | bal. |

Formulation Example 2

Protector

| (Constitutive Ingredients) | (% by mass) |
|---|---|
| (1) Cetanol | 1 |
| (2) Glycerin | 5 |
| (3) 1,3-Butylene glycol | 5 |
| (4) Polyethylene glycol 20000 | 2 |
| (5) Pentaerythritol tetra (2-ethylhexanoate/parametoxycinnamate) | 3 |
| (6) Di-2-ethylhexyl succinate | 3 |
| (7) Sodium hydroxide | q. s. |
| (8) Trisodium edetate | 0.1 |
| (9) Methylbis (trimethylsiloxy) silylisopentyl trimethoxycinnamate | 2 |
| (10) 4-T-buty1-4'-methoxydibenzeylmethane | 2 |
| (11) 2-Ethylhexyl parametnoxycinnamate | 2 |
| (12) Glyceryl diparamethoxycinnamate mono-2-ethylhexanoate | 2 |
| (13) Hydrophobic denatured polyether urethane | 0.5 |
| (14) Gellan gum microgel | 0.25 |
| (15) Acrylic acid/alkyl methacrylate copolymer ("Pemulen TR-1") | 0.1 |
| (16) Paraben | q. s. |
| (17) Phenoxyethanol | q. s. |
| (18) Pure water | bal. |
| (19) Fragrance | q. s. |

Formulation Example 3

Skin Milk

| (Constitutive Ingredients) | (% by mass) |
|---|---|
| (1) Vaseline | 5 |
| (2) Behenyl alcohol | 0.5 |
| (3) Batyl alcohol | 0.5 |
| (4) Glycerin | 7 |
| (5) 1,3-Butylene glycol | 7 |
| (6) 1,2-Pentanediol | 1 |
| (7) Xylitol | 3 |
| (8) Polyethylene glycol 20000 | 2 |
| (9) Hardened oil | 2 |
| (10) Jojoba oil | 2 |
| (11) Squalane | 5 |
| (12) Isostearic acid | 0.5 |
| (13) Pentaerythritol tetra-2-ethylhexanoate | 2 |
| (14) Polyoxyethylene-hardened castor oil | 0.5 |
| (15) Betaine lauryldimethylaminoacetate | 0.4 |
| (16) Sodium pyrosulfite | 0.01 |
| (17) Sodium hexametaphosphate | 0.05 |
| (18) Dipotassium glycyrrhizinate | 0.05 |
| (19) Trimethylglycine | 3 |
| (20) Arbutin | 3 |
| (21) Yeast extract | 0.1 |
| (22) Tocopherol acetate | 0.1 |
| (23) Thiotaurine | 0.1 |
| (24) Scophora angustifolia root extract | 0.1 |
| (25) Red iron oxide | q. s. |
| (26) Pyrus Cydonia seed extract | 0.1 |
| (27) Hydrophobic denatured polyether urethane | 0.2 |
| (28) Agar microgel | 1.0 |
| (29) Phenoxyethanol | q. s. |
| (30) Pure water | bal. |

Formulation Example 4

Transparent Gel

| (Constitutive Ingredients) | (% by mass) |
|---|---|
| (1) Water-soluble collagen | 1.5 |
| (2) Dipropylene glycol | 7.0 |
| (3) Polyethylene glycol 1500 | 8.0 |

-continued

| (Constitutive Ingredients) | (% by mass) |
|---|---|
| (4) Hydrophobic denatured polyether urethane | 0.5 |
| (5) Gellan gum microgel | 0.5 |
| (6) POE (15 mol) oleyl ether | 1.0 |
| (7) Potassium 4-methoxysalicylate | 1.0 |
| (8) Methylparaben | q. s. |
| (9) Discoloration inhibitor | q. s. |
| (10) Colorant | q. s. |
| (11) Edetate salt | q. s. |
| (12) Fragrance | q. s. |
| (13) Pure water | bal. |

Formulation Example 5

Essence Gel

| (Constitutive Ingredients) | (% by mass) |
|---|---|
| (1) Dimethylsiloxane | 5 |
| (2) Glycerin | 2 |
| (3) 1,3-Butylene glycol | 5 |
| (4) Polyethylene glycol 1500 | 3 |
| (5) Polyethylene glycol 20000 | 3 |
| (6) Cetyl octenoate | 3 |
| (7) Citric acid | 0.01 |
| (8) Sodium citrate | 0.1 |
| (9) Sodium hexametaphosphate | 0.1 |
| (10) Dipotassium glycyrrhizinate | 0.1 |
| (11) Ascorbic acid glucoside | 2 |
| (12) Tocopherol acetate | 0.1 |
| (13) Scutellaria root extract | 0.1 |
| (14) Saxifrage extract | 0.1 |
| (15) Trisodium edetate | 0.1 |
| (16) Xanthane gum | 0.3 |
| (17) Acrylic acid/alkyl methacrylate copolymer ("Pemulen TR-2") | 0.05 |
| (18) Hydrophobic denatured polyether urethane | 0.5 |
| (19) Agar microgel | 1.5 |
| (20) Phenoxyethanol | q. s. |
| (21) Dibutylhydroxytoluene | q. s. |
| (22) Pure water | bal. |

Formulation Example 6

Whitening Milk

| (Constitutive Ingredients) | (% by mass) |
|---|---|
| (1) Vaseline | 5 |
| (2) Behenyl alcohol | 0.5 |
| (3) Batyl alcohol | 0.5 |
| (4) Glycerin | 7 |
| (5) 1,3-Butylene glycol | 7 |
| (6) 1,2-Pentanediol | 1 |
| (7) Xylitol | 3 |
| (8) Polyethylene glycol 20000 | 2 |
| (9) Hardened oil | 2 |
| (10) Jojoba oil | 2 |
| (11) Squalane | 5 |
| (12) Isostearic acid | 0.5 |
| (13) Pentaerythritol tetra-2-ethylhexanoate | 2 |
| (14) Polyoxyethylene-hardened castor oil | 0.5 |
| (15) Betaine lauryldimethylaminoacetate | 0.4 |
| (16) Sodium pyrophosphate | 0.01 |
| (17) Sodium hexametaphosphate | 0.05 |
| (18) Dipotassium glycyrrhizinate | 0.05 |
| (19) Trimethylglycine | 3 |
| (20) Ascorbic acid glucoside | 2 |

-continued

| (Constitutive Ingredients) | (% by mass) |
|---|---|
| (21) Tocopherol acetate | 0.1 |
| (22) Thiotaurine | 0.1 |
| (23) Red iron oxide | q. s. |
| (24) Pyrus Cydonia seed extract | 0.1 |
| (25) Hydrophobic denatured polyether urethane | 0.25 |
| (26) Gellan gum microgel | 0.25 |
| (27) Phenoxyethanol | q. s. |
| (28) Pure water | bal. |

Formulation Example 7

Face Wash

| (Constitutive Ingredients) | (% by mass) |
|---|---|
| (1) Glycerin | 6 |
| (2) 1,3-Butylene glycol | 4 |
| (3) Polyethylene glycol 400 | 13 |
| (4) Bleached bees wax | 0.5 |
| (5) Stearic acid | 20 |
| (6) Lauric acid | 5 |
| (7) Myristic acid | 10 |
| (8) POE (25) POP glycol(30) | 0.5 |
| (9) Self-emulsifying glycerin monostearate | 2 |
| (10) Titanium oxide | 0.2 |
| (11) Sodium citrate | 0.05 |
| (12) Potassium hydroxide | 6.5 |
| (13) Hydrophobic denatured polyether urethane | 0.3 |
| (14) Agar microgel | 0.8 |
| (15) Chamomilla extract | 0.1 |
| (16) Trisodium edetate | q. s. |
| (17) Pure water | bal. |
| (18) Fragrance | q. s |

Formulation Example 8

Foundation

| (Constitutive Ingredients) | (% by mass) |
|---|---|
| (1) Behenyl alcohol | 0.5 |
| (2) Dipropylene glycol | 6 |
| (3) Stearic acid | 1 |
| (4) Glycerin monostearate | 1 |
| (5) Potassium hydroxide | 0.2 |
| (6) Triethanolamine | 0.8 |
| (7) DL-α-tocopherol acetate | 0.1 |
| (8) Parahydroxybenzoate | q. s. |
| (9) Yellow iron oxide | 1 |
| (10) α-olefin oligomer | 3 |
| (11) Dimethylpolysiloxane (6 mPa · s) | 2 |
| (12) Dimethylpolysiloxane (100 mPa · s) | 5 |
| (13) Batyl alcohol | 0.5 |
| (14) Isostearic acid | 1 |
| (15) Behenic acid | 0.5 |
| (16) Cetyl 2-ethylhexanoate | 10 |
| (17) Polyoxyethylene glycerin monostearate | 1 |
| (18) Titanium oxide | 3 |
| (19) Mica titanium/polyalkyl acrylate composite powder | 0.5 |
| (20) Surface-treated titanium oxide (MT-062) | 10 |
| (21) Polyalkyl acrylate-coated mica titanium | 0.5 |
| (22) Black iron oxide-coated mica titanium | 0.5 |
| (23) Silicic anhydride | 6 |
| (24) 2-Ethylhexyl paramethoxycinnamate | 2 |
| (25) Red iron oxide | q. s. |
| (26) Ultramarine | q. s. |
| (27) Black iron oxide | q. s. |

-continued

| (Constitutive Ingredients) | (% by mass) |
|---|---|
| (28) Certified color | q. s. |
| (29) Hydrophobic denatured polyether urethane | 0.8 |
| (30) Gellan gum microgel | 0.2 |
| (31) Bentonite | 1 |
| (32) Sodium carboxymethyl cellulose | 0.1 |
| (33) Pure water | bal. |
| (34) Fragrance | q. s. |

Industrial Applicability

The thickening composition and the cosmetic containing the composition of the invention are excellent in feelings in use, namely, excellent in freshness, non-stickiness and blend into skin feeling, not leaving any residue on skin, and can stably keep the viscosity thereof in a low- to moderate-level viscosity range.

The invention claimed is:

1. A cosmetic preparation that contains a thickening composition comprising:
   (a) from 0.1 to 2% by mass of a hydrophobic denatured polyether urethane represented by the following formula (I),

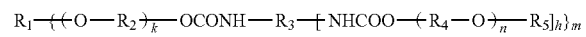
(I)

wherein $R_1$, $R_2$ and $R_4$ each independently represent an alkylene group having from 2 to 4 carbon atoms, or a phenylethylene group; $R_3$ represents an alkylene group having from 1 to 10 carbon atoms and optionally having an urethane bond; $R_5$ represents a linear, branched or secondary alkyl group having from 8 to 36 carbon atoms; m indicates a number of 2 or more; h indicates a number of 1 or more; k indicates a number of from 1 to 500; and n indicates a number of from 1 to 200; and
   (b) from 0.1 to 2% by mass of a microgel to be obtained by grinding a gel of a hydrophilic compound having a gelling capability, characterized in that the hydrophilic compound is agar and/or gellan gum,
wherein a mass ratio of component (a)/component (b) is from 0.1/0.9 to 0.9/0.1, and the thickening composition has a viscosity of from 50 to 50,000 mPa·s as measured with a BL-type viscometer operated at 12 rotations per minute and 25° C.

2. The cosmetic preparation as claimed in claim 1, wherein $R_1$, $R_2$ and $R_4$ in the formula (I) each independently represent an alkylene group having from 2 to 4 carbon atoms, $R_3$ represents an alkylene group having from 1 to 10 carbon atoms and optionally having an urethane bond, $R_5$ represents a linear, branched or secondary alkyl group having from 12 to 24 carbon atoms, m is 2, h is 1, k is a number of from 100 to 300, and n is a number of from 10 to 100.

3. The cosmetic preparation as claimed in claim 1, wherein component (b) is a microgel having a mean particle size of from 0.1 to 1,000 µm, as prepared by grinding a gel formed by dissolving agar and/or gellan gum in water or in an aqueous component followed by keeping it cooled.

4. The cosmetic preparation as claimed in claim 1, which further contains pharmaceutical ingredients, salts, or combinations thereof.

5. The cosmetic preparation as claimed in claim 2, wherein component (b) is a microgel having a mean particle size of from 0.1 to 1,000 µm, as prepared by grinding a gel formed by dissolving agar and/or gellan gum in water or in an aqueous component followed by keeping it cooled.

6. The cosmetic preparation as claimed in claim 2, which further contains pharmaceutical ingredients, salts, or combinations thereof.

7. The cosmetic preparation as claimed in claim 3, which further contains pharmaceutical ingredients, salts, or combinations thereof.

* * * * *